United States Patent [19]

Kesling, Jr.

[11] Patent Number: 4,514,576

[45] Date of Patent: Apr. 30, 1985

[54] PRODUCTION OF ARYL ALKYL ETHERS FROM METHYLBENZYL ALCOHOL USING RHENIUM HEPTOXIDE CATALYST

[75] Inventor: Haven S. Kesling, Jr., Drexel Hill, Pa.

[73] Assignee: Atlantic Richfield Company, Los Angeles, Calif.

[21] Appl. No.: 510,022

[22] Filed: Jul. 1, 1983

[51] Int. Cl.$^3$ .............................................. C07C 41/09
[52] U.S. Cl. .................................... 568/659; 568/631
[58] Field of Search ................................ 568/659, 631

[56] References Cited

U.S. PATENT DOCUMENTS 3,769,351 10/1973 Mukai .................................. 568/659

FOREIGN PATENT DOCUMENTS 47-26497 7/1972 Japan .................................. 568/659

OTHER PUBLICATIONS

Mikhalev et al., Chem. Abs., vol. 55 (1961), 3524.

*Primary Examiner*—Bernard Helfin
*Attorney, Agent, or Firm*—Dennis M. Kozak

[57] ABSTRACT

The synthesis of aryl alkyl ethers from methylbenzyl alcohol and, optionally, phenol using a rhenium heptoxide catalyst is disclosed.

11 Claims, No Drawings

PRODUCTION OF ARYL ALKYL ETHERS FROM METHYLBENZYL ALCOHOL USING RHENIUM HEPTOXIDE CATALYST

This invention relates to aryl alkyl ethers.

More specifically, this invention relates to the use of a rhenium heptoxide catalyst for the production of aryl alkyl ethers from methylbenzyl alcohol, and optionally, phenol.

Aryl alkyl ethers, such as α-phenylmethylbenzyl ether, have found application in the fields of heat transfer fluids, pesticides, dyestuffs, odor substances, antioxidants, plastic additives, and general solvent usage.

Although many methods are known for the preparation of aryl alkyl ethers, see for example U.S. Pat. No. 4,299,996, their synthesis from methylbenzyl alcohol, using acid or base catalysis, has not been very successful. Traditional methods of synthesis involving acid or base catalysis fail due to facile dehydration of the methylbenzyl alcohol used as a starting material. The result is little or no aryl alkyl ether and a high styrene yield.

The catalyst of this invention (see Eq. No. 1), while giving some styrene, affords primarily aryl alkyl ether products.

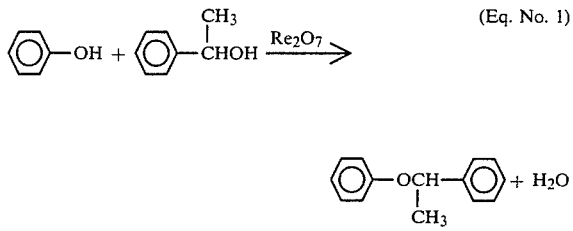

(Eq. No. 1)

Traditional methods of synthesis involving acid or base catalysis (Eq. No. 2) result in little aryl alkyl ether and a high styrene yield.

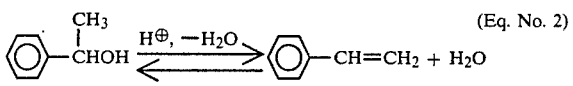

(Eq. No. 2)

According to the present invention there is provided an improved process for the catalytic preparation of bis-methylbenzyl ether from methylbenzyl alcohol wherein the improvement comprise using rhenium heptoxide as the catalyst.

Also, according to the present invention, there is provided an improved process for the catalytic preparation of α-phenylmethylbenzyl ether and bis-methylbenzyl ether from phenol and methylbenzyl alcohol in the presence of a catalyst wherein the improvement comprises using rhenium heptoxide as the catalyst.

Besides the advantage of forming high ether yields, there are several more subtle advantages offered by the improved process of this invention. The advantages include decreased corrosion, more simplified work-ups, and the elimination of alkali metal salt disposal problems which would be associated with a traditional Williamson synthesis or neutralization of an acid catalyst. Moreover, in the process of this invention, the product ethers are easily separated from the catalyst by distillation and, the catalyst heal can be recycled.

In the practice of this invention, the operative reaction conditions can be selected to be within wide ranges. Preferably, the following reaction conditions will be within the range specified; reaction temperature 75° to 150° C., residence time 1 to 10 hours, reactor pressure 200 to 2280 mm Hg.

The reactants employed in the process of this invention will be employed in an amount within the following weight percent ranges; methylbenzyl alcohol 15 to 20, phenol 0 to 30, solvent 25 to 85 and rhenium heptoxide 0.01 to 0.5. If phenol is employed, it will preferably be employed in an amount within the range of from about 10 to about 30 weight percent and the solvent weight percent reduced accordingly.

As the solvent, any suitable aromatic or hydrocarbon solvent can be employed and should be selected based on boiling point. Suitable solvents include benzene, toluene, ethylbenzene, cumene, heptene, decane, and the like, and their mixtures. The preferred solvent is ethylbenzene.

The following examples serve to further demonstrate the invention.

EXAMPLE I (Control)

Phenol (21.21 grams; 0.25 mole) and methylbenzyl alcohol (30.5 grams; 0.25 mole) in 100.00 grams of ethylbenzene were refluxed at a temperature of from about 135° to 140° C. for about four hours with 0.500 grams (0.33 weight percent) concentrated sulfuric acid. Water was removed overhead as a azeotrope and was collected in a Dean-Stark trap. Methylbenzyl alcohol conversion was quantitative but only 8% selectivity to α-phenylmethylbenzyl ether was obtained. The remaining product was styrene (74.8% selectivity) and styrene polymer.

EXAMPLE II

This example demonstrates the use of rhenium heptoxide catalyst in the preparation of aryl alkyl ethers according to this invention.

Phenol (21.21 grams; 0.25 mole) and methylbenzyl alcohol (30.5 grams; 0.25 mole) in 100.00 grams of ethylbenzene were refluxed at a temperature of from about 135° to 140° C. for about two hours with 0.15 gram; rhenium heptoxide. Water was removed overhead as an azeotrope and was collected in a Dean-Stark trap. Methylbenzyl alcohol conversion was 93.7%. Selectivity to α-phenylmethylbenzyl ether, bis-methyl benzyl ether and styrene was 72.1%, 8.5% and 19.4% respectively.

EXAMPLE III

This example demonstrates the use of rhenium heptoxide catalyst in the prepartion of aryl alkyl ethers according to this invention. No phenol was employed.

Methylbenzyl alcohol (61.00 grams; 0.50 mole) in 100.00 grams of ethylbenzene were refluxed at a temperature of from about 135° to 140° C. for about two hours with 0.17 gram rhenium heptoxide. Water was removed overhead as an azeotrope and was collected in a Dean-Stark trap. Methylbenzyl alcohol conversion was 93.3%. Selectivity to bis-methylbenzyl ether and styrene was 68.7% and 31.3% respectively.

EXAMPLE IV

This example demonstrates the use of rhenium heptoxide catalyst in the preparation of aryl alkyl ethers according to this invention. No phenol was employed.

Methylbenzyl alcohol (61.00 grams; 0.50 mole) in 100.00 grams of benzene were refluxed at a temperature of from about 80°–85° C. for about four hours with 1000 ppm (0.016 gram) rhenium heptoxide. Water was removed overhead as an azeotrope and was collected in a Dean-Stark trap. Methylbenzyl alcohol conversion was 69.5%. Selectivity to bis methylbenzylether and styrene was 88.6% and 11.4%, respectively.

The following Table illustrates the reactions conditions, % conversion and % selectivity of the preceeding four examples:

TABLE

| Example No. | 1 (Control) | 2 | 3 | 4 |
|---|---|---|---|---|
| Reaction Conditions | | | | |
| Temperature (°C.) | 135 | 135 | 135 | 80 Reflux |
| Time (hrs) | 4 | 2 | 2 | 4 |
| Solvent | EB | EB | EB | Benz. |
| Catalyst (Wt %) | $H_2SO_4$/.33 | $Re_2O_7$/.1 | $Re_2O_7$/.1 | $Re_2O_7$/ 1000 ppm |
| % Conversion (on MBA) | 100 | 93.7 | 98.3 | 69.5 |
| % Selectivity (on MBA) | | | | |
| PMBE | 8 | 72.1 | — | — |
| DMBE | — | 8.5 | 68.7 | 88.6 |
| Styrene | 74.8 | 19.4 | 31.3 | 11.4 |

Notes:
Solvents: EB = ethylbenzenes
Benz = benzene
Products: Gas chromotography was used to determine product composition.
PMBE = α-phenylmethylbenzyl ether (b.p. 86–87° C./0.3 mm Hg isolated by distillation)
DMBE = bis-methylbenzyl ether (b.p. 93° C./0.7 mm Hg isolated by distillation)

It will be evident from the foregoing that various modifications can be made to this invention. Such, however, are considered within the scope of this invention.

What is claimed is:

1. An improved process for the catalytic preparation of bis alpha-methylbenzyl ether from alpha-methylbenzyl alcohol in the presence of a catalyst wherein the improvement comprises contacting said alpha-methylbenzyl alcohol with a rhenium heptoxide catalyst.

2. The process of claim 1 in which said alpha-methylbenzyl alcohol is present in an amount within the range of from about 15 to about 20 weight percent.

3. The process of claim 1 in which said solvent is selected from the group consisting of at least one of benzene, toluene, ethylbenzene, cumene, heptane and decane.

4. The process of claim 1 in which said solvent is present in an amount within the range of from about 25 to about 85 weight percent.

5. The process of claim 1 in which said rhenium heptoxide catalyst is present in an amount within the range of from about 0.01 to about 0.5 weight percent.

6. An improved process for the catalytic preparation of bis alpha-methylbenzyl ether and α-phenylmethylbenzey ether from alpha-methylbenzyl alcohol and phenol wherein the improvement comprises contacting said alpha-methylbenzyl alcohol and said phenol with a rhenium heptoxide catalyst.

7. The process of claim 6 in which said phenol is present in an amount within the range of from about 10 to about 30 weight percent.

8. The process of claim 6 in which said alpha-methylbenzyl alcohol is present in an amount within the range of from about 15 to about 20 weight percent.

9. The process of claim 6 in which said solvent is selected from the group consisting of at least one of benzene, toluene, ethylbenzene, cumene, heptane and decane.

10. The process of claim 6 in which said solvent is present in an amount within the range of from about 25 to about 75 weight percent.

11. The process of claim 6 in which said rhenium heptoxide catalyst is present in an amount within the range of from about 0.01 to about 0.5 weight percent.

* * * * *